United States Patent
Williams et al.

(10) Patent No.: US 6,701,254 B1
(45) Date of Patent: Mar. 2, 2004

(54) METHOD FOR ANALYZING SAMPLES OF BIOMOLECULES IN AN ARRAY

(75) Inventors: Keith Leslie Williams, Frenchs Forest (AU); Nicolle Hannah Packer, Gordon (AU); Andrew Arthur Gooley, Turramurra (AU)

(73) Assignee: Proteome Systems, Limited, North Ryde (AU)

(*) Notice: Subject to any disclaimer, the term of this patent is extended or adjusted under 35 U.S.C. 154(b) by 0 days.

(21) Appl. No.: 09/403,196

(22) PCT Filed: Apr. 16, 1998

(86) PCT No.: PCT/AU98/00265

§ 371 (c)(1),
(2), (4) Date: Dec. 17, 1999

(87) PCT Pub. No.: WO98/47006

PCT Pub. Date: Oct. 22, 1998

(30) Foreign Application Priority Data

Apr. 16, 1997 (AU) .............................................. PO 6254

(51) Int. Cl.[7] .............................................. G01N 21/00
(52) U.S. Cl. .............................. 702/22; 702/19; 702/30; 436/164; 422/82.05
(58) Field of Search .............................. 702/19–23, 25, 702/27, 28, 30–32, 127, 183, FOR 170, FOR 115–FOR 119, FOR 121, FOR 131, FOR 134, FOR 141; 700/266–269, 273, 285; 422/30, 62, 67, 68.1, 70, 79, 82.05, 82.07, 82.08; 435/287.1, 287.3; 436/43, 46, 47, 50, 51, 55, 63, 164–166, 169–172, 805, 807, 808; 382/128–130, 133, 134; 204/600–608, 610, 612, 613, 400, 406, 407, 403.01, 403.15, 556, 45.6; 250/461.1, 461.2, 458.1, 309, 311, 339.02, 339.07–339.09, 339.12; 356/300–303, 319, 326, 432, 440, 306

(56) References Cited

U.S. PATENT DOCUMENTS

| | | | |
|---|---|---|---|
| 4,877,745 A | 10/1989 | Hayes et al. ................. | 436/166 |
| 4,960,999 A | 10/1990 | McKean et al. .......... | 250/461.1 |
| 5,273,877 A | * 12/1993 | Fey et al. ...................... | 436/63 |
| 5,534,121 A | * 7/1996 | Merrick et al. ............. | 204/613 |
| 5,667,656 A | * 9/1997 | Kambara .................. | 250/461.2 |
| 5,671,086 A | 9/1997 | Parvin et al. | |
| 5,993,634 A | * 11/1999 | Simpson et al. ............ | 204/600 |
| 6,007,231 A | * 12/1999 | Vijg et al. .................... | 702/20 |
| 6,090,545 A | * 7/2000 | Wohlstadter et al. ....... | 204/400 |

FOREIGN PATENT DOCUMENTS

| | | | |
|---|---|---|---|
| EP | 646 784 A1 | 4/1995 | .......... G01N/21/86 |
| WO | WO96/09600 | 3/1996 | ............ G06K/9/00 |
| WO | WO 97/44134 | 11/1997 | |
| WO | WO98/07022 | 2/1998 | .......... G01N/21/64 |
| WO | WO 98/23950 | 6/1998 | |
| WO | WO 00/79238 A1 | 12/2000 | |
| WO | WO 02/075321 A1 | 9/2002 | |

* cited by examiner

*Primary Examiner*—Hal Wachsman
(74) *Attorney, Agent, or Firm*—Hamilton, Brook, Smith & Reynolds, P.C.

(57) ABSTRACT

Described is a method for analyzing at least one sample in an array of samples, the method including recording an image of the position of at least one sample relative to the other sample; utilizing the recorded image to allow the application of a reagent or a succession of reagents to at least one sample in situ; and analyzing at least one sample for a reaction with the reagent(s). Also described is an apparatus for analyzing at least one sample in an array of samples, the apparatus including (a) a device to record an image of the position of at least one sample relative to the other samples; (b) a device to apply a reagent or sequence of reagents to at least one sample in situ; (c) a device to analyse at least one sample for a reaction with the reagent(s); and (d) a device to control the application of reagent(s) to the samples.

46 Claims, 6 Drawing Sheets

METHOD FOR ANALYZING SAMPLES OF BIOMOLECULES IN AN ARRAY

TECHNICAL FIELD

The present invention relates to methods for analysing one or more samples in an array of samples, preferably biomolecules, and an apparatus for carrying out these methods.

BACKGROUND ART

Improvements in laboratory techniques and practices have led to the discovery of an ever increasing number of new biomolecules. New protein purification and detection methods, for example, have allowed the detection of many possibly new proteins. Due to the large number of known biomolecules, it is now necessary to carry out molecular comparisons of newly discovered molecules to determine to what extent they are similar to or different from known molecules. To carry out definitive analyses for proteins for example it is necessary to obtain amino acid sequence information. Unfortunately, current methods and apparatus for such analyses are slow and are only able to analyse one or a few samples at one time. In order to carry out analysis of a given protein at present it is necessary to obtain the protein in substantially pure and isolated form. There is a need for methods and apparatus that can analyse one desired sample from an array of samples or be able to analyse multiple samples.

The present inventors have now realised that it is possible to develop improved methods and apparatus suitable to carry out these types of analyses.

DISCLOSURE OF INVENTION

The present invention relates generally to methods for analysing at least one sample in an array of samples by recording an image of the position of at least one sample relative to the other samples in the array and utilizing the recorded image so as to allow the analysis of the at least one sample in situ.

In a first aspect, the present invention consists of a method for analysing at least one sample in an array of samples, the method including the steps:

(a) recording an image of the position of at least one sample relative to the other samples in the array;

(b) utilizing the recorded image so as to allow the application of a reagent or a succession of reagents to the at least one sample in situ; and (c) analysing the at least one sample for a reaction to or with the reagent(s).

In a preferred form, the samples are biomolecules selected from the group consisting of proteins, peptides, saccharides, lipids, nucleic acid molecules, complex biomolecules including glycoproteins, and mixtures thereof. The biomolecules are preferably separated by chromatography to form an array of samples. The chromatography is preferably electrophoresis, and more preferably electrophoresis is carried out in a polyacrylamide gel.

The polyacrylamide gel electrophoresis can be carried out in one dimension including isoelectric focusing, native polyacrylamide gel electrophoresis, and sodium dodecyl sulfate (SDS) polyacrylamide gel electrophoresis. Alternatively, the polyacrylamide gel electrophoresis is carried out in two dimensions with the first dimension by isoelectric focusing and the second dimension is by SDS polyacrylamide gel electrophoresis.

Preferably, the biomolecules separated by electrophoresis are transferred to a semi-solid or solid support. The solid support can be a membrane made of polyvinylidene difluoride, nitrocellulose, nylon, Teflon™, Zitex™, polypropylene, polytetrafluoroethylene, and derivatised forms thereof having one or more functional groups.

Preferably, the biomolecules transferred to semi-solid or solid support are visualised by association with a dye, fluorescent group or metal, or by association with a second biomolecule which is coupled with a third biomolecule, dye, fluorescent group or metal. The array of samples is preferably in a plane in order to assist in the recording of the image.

In a preferred embodiment of the present invention, the image is generated from a scan of the samples stained or illuminated to allow them to be visualised and the application of the reagent or reagents is carried out using a chemical printer based on an "ink jet" or similar application system where the reagent or reagents are discharged to the desired sample by the chemical printer.

It will be appreciated that the array to be manipulated may not necessarily be the array from which the image was obtained. For example, it would be possible to make multiple identical arrays of samples and use one array to obtain the image but use one or more of the multiple identical arrays to carry out the manipulations. For example in protein separation by 2 dimension polyacrylamide gel electrophoresis (2D PAGE) one separation gel may be blotted to more than one support or multiple identical separations carried out and each transferred to a support to form the identical arrays.

The analysing may be by any means known to the art. Suitable examples include use of liquid chromatograph, photoelectrical, photochemical, laser, radiochemical, and mass spectral analyses. The sample may be analysed directly for a given reaction product. Alternatively, where reagent has been applied to one sample in the array and has reacted with the one of the sample treated, it would be possible to analyse the array of samples and the detection of a reaction product would be assigned as being derived from the one sample treated.

The image can be recorded by any suitable means including recorded as an electronic or digital image. In one preferred form, the image is generated from a scan of the samples stained or illuminated to allow the samples to be visualised and the application of the reagent or reagents is carried out using a chemical printer application system where the reagent or reagents are discharged to the desired sample by the chemical printer.

It will be appreciated that steps (a) and (b) can be repeated or cycled so as to carry out a series of manipulations of the same sample or a number of different samples in the array. The multiple manipulations can be with the same reagent, the same set of reagents, or a number of different reagents.

The analysing is preferably by liquid chromatography, photoelectrical, photochemical, laser, radiochemical, or mass spectral analyses. It will be appreciated that the sample can be analysed directly for a given reaction product.

In order to generate an image of the samples in the array, it is usually necessary to make them identifiable in some manner. Labelling the samples with a visible marker is one example that would allow the visualisation of the position of the samples with a charged coupled device (CCD). A scan of the labelled samples would then be recorded digitally and stored in a computer for example. Once the image has been recorded in digital form for example, there would be no need to maintain the visualisation of the samples on the array as the image is maintained electronically. If the locations of the samples are recorded on an X/Y grid, this would be one way of accessing the positions of the samples electronically or digitally. The computer would also control the application of the reagent in step (b) to the position of the sample to be manipulated. The amount of chemical delivered to a sample would be regulated in the same manner as grey-scale for black and white printing. The position of all the samples would be known from their co-ordinates on the grid, for example, and so further manipulation is possible regardless of whether or not the samples are still visible.

The present invention is particularly suitable for the multiple analyses of one or more samples, particularly on an array like a protein blot. The method is applicable for N- and C-terminal determination of proteins and peptides derived from proteins separated by, for example, two dimensional gel electrophoresis. It will be appreciated that the method can be used for antibody or antigen assays of multiple samples and the like and the present method makes possible the different subsequent steps based on the outcome of an earlier reaction.

In one preferred form, the invention concerns the development of a chemical printer which sprays a chemical reagent to a sample which has been absorbed onto a solid support so as to cause a detectable reaction with the molecules in the sample. The analysis of a chemical derivative of the molecules of the sample can be by laser desorption ionisation while it is still absorbed on the support. Furthermore, it is possible to analyse a different part of the same sample following each cycle of chemistry since the laser desorption technology can be aimed accurately at different regions of the sample.

A suitable chemical printing system for use in the present invention involves the use of piezoelectric drop-on-demand ink-jet printing technology for microdispensing fluids in DNA diagnostics or the Combion, Inc. synthesis process called "Chem-jet". To explore drop-on-demand fluid dispensing for DNA diagnostics, an eight fluid printer has been developed as part of the Genosensor Technology Development (GTD) project funded by the National Institute of Standards and Technology (USA). Research to date has focused on "printing" oligonucleotide microspots onto solid supports. In the "Chem-jet" technique, which was developed at the California Institute of Technology, tiny volumes of reagent-bearing liquid are squirted onto specific spots, or addresses, of a solid substrate much as an ink-jet printer squirts tiny dots onto a page. By repeatedly returning to each address with one or another of a small set of building blocks, in this case nucleotides modified for the process, huge two-dimensional libraries of short DNA chains (oligonucleotides) can be assembled.

The GTD and "Chem-jet" are sensor/synthesis instruments rather than analysers. Hence, the present invention embraces a new application for the ink jet assembly technology.

It will be appreciated that many different chemistries can be performed in situ on samples on supports, particularly for proteins, in light of the recent developments of micro-preparative immobilised pH gradient isoelectric focusing. Laboratory examples include the enzymic digests of visualised protein spots, the enzymic and chemical release of oligosaccharides attached to stained protein spots, and antibody/antigen reactions. It will be appreciated that such analyses can be conducted sequentially by the chemical printer. A further application of the chemical printer is large scale Edman chemistry and C-terminal chemistry on all proteins separated by two-dimensional electrophoresis.

Many additional permutations of the printer are possible:

i) The analysis of peptides after endoproteinase digests of a single (or small number) of proteins where, following a cycle of Edman chemistry, the released amino acids from each cycle of chemistry are analysed using laser desorption TOF-MS in combination with bioinformatics approach to identify the protein.

ii) Other macromolecules, for example complex carbohydrates and lipids which have been separated on thin layer chromatography or other supports.

iii) For blocked proteins, detected by absence of an amino acid after printing the first cycle of Edman chemistry, the support is then printed with an endoproteinase. Following the digest, the support is then subjected to a 'printing' of an end group blocking reagent which is specific for a particular sequence motif. For example, following an endoproteinase Asp-N digestion and one cycle (or 'printing') of Edman chemistry, the support is printed with o-phthalaldehyde (OPA), which blocks all $\alpha$-amino groups leaving only peptides with an N-terminal Pro. Hence, the process is specific for the motif Asp-Pro. Alternatively, following the trypsin digest, a cycle of Edman chemistry and a printing of OPA, the process is specific for the motif Lys/Arg-Xaa-Pro. These unblocked peptides can be analysed according to (i) above.

In a second aspect, the present invention consists in an apparatus for carrying out the first aspect of the present invention.

An apparatus for analysing at least one sample in an array of samples, the apparatus including:

(a) means for recording an image of the position of the at least one sample relative to the other samples in the array;

(b) means for applying a reagent or sequence of reagents to the at least one sample in situ;

(c) means for analysing the at least one sample for a reaction to or with the reagent(s); and (d) control means for means (b), wherein means (b) applies the reagent to the at least one sample according to the position of the sample relative to the other samples in the array determined by means (a).

The apparatus may further include means for recording the analysis results obtained by means (c).

Preferably, the means (a) is selected from the group consisting of scanner, photodetector, and charged coupled device.

Means (b) may be a chemical printer adapted to apply one or more reagents to the sample. Alternatively, means (b) is a reagent delivery and extraction device including a fluid source, a fluid control means, a fluid delivery and sampling device for delivering fluid to a sample in the array and for sampling fluid applied to the sample on the array, and an extraction device capable of retaining a reaction product from a sample on the array; a control device for controlling fluid movement from the fluid source to the fluid delivery and sampling device and for controlling fluid movement from the sample to the extraction device via the fluid delivery and sampling device; wherein, in use, fluid capable of producing a reaction product from a sample is applied to a sample on the array from the fluid source via the fluid control means to the fluid delivery and sampling device by the action of the control device, and wherein a portion of the fluid applied to the sample is drawn through the fluid delivery and sampling device to the extraction device by the action of the control device.

The extraction device is not necessary for the present invention but may be useful when certain analyses of treated samples are required. For example, the extraction device is particularly suitable for introducing a sample into an electrospray mass spectrometer. The extraction device, however, may not be necessary for introducing the sample into the MALDI-TOF as this instrument is much more tolerant of salts.

Preferably the fluid control means is a 3-way valve.

Preferably, the control device comprises a first control device for the fluid delivery and sampling device and a second control device for the extraction device. More preferably, the first and second control devices are piezoelectric control devices.

The fluid is preferably a reagent capable of reacting with a sample to produce a detectable product capable of being retained by the extraction device. The extraction device is preferably a cartridge of chromatography packing.

In a preferred form means (c) is selected from the group consisting of liquid chromatograph, photoelectrical detector, photochemical detector, laser detector, radiochemical detector, and mass spectrometer. Means (d) can be a computer programmed to control means (b).

The array of samples is preferably on a semi-solid or substantially solid support. One advantage of the present invention is that very small samples may be treated and analysed. The apparatus according to the present invention is particularly suitable for analysing samples having an area less than about 100 mM$^2$, preferably less than about 50 mm$^2$, more preferably about 1 to 10 mm$^2$. It will be appreciated, however, that even smaller samples may be analysed by the present invention.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and accompanying drawings.

MODES FOR CARRYING OUT THE INVENTION

Figure 1:
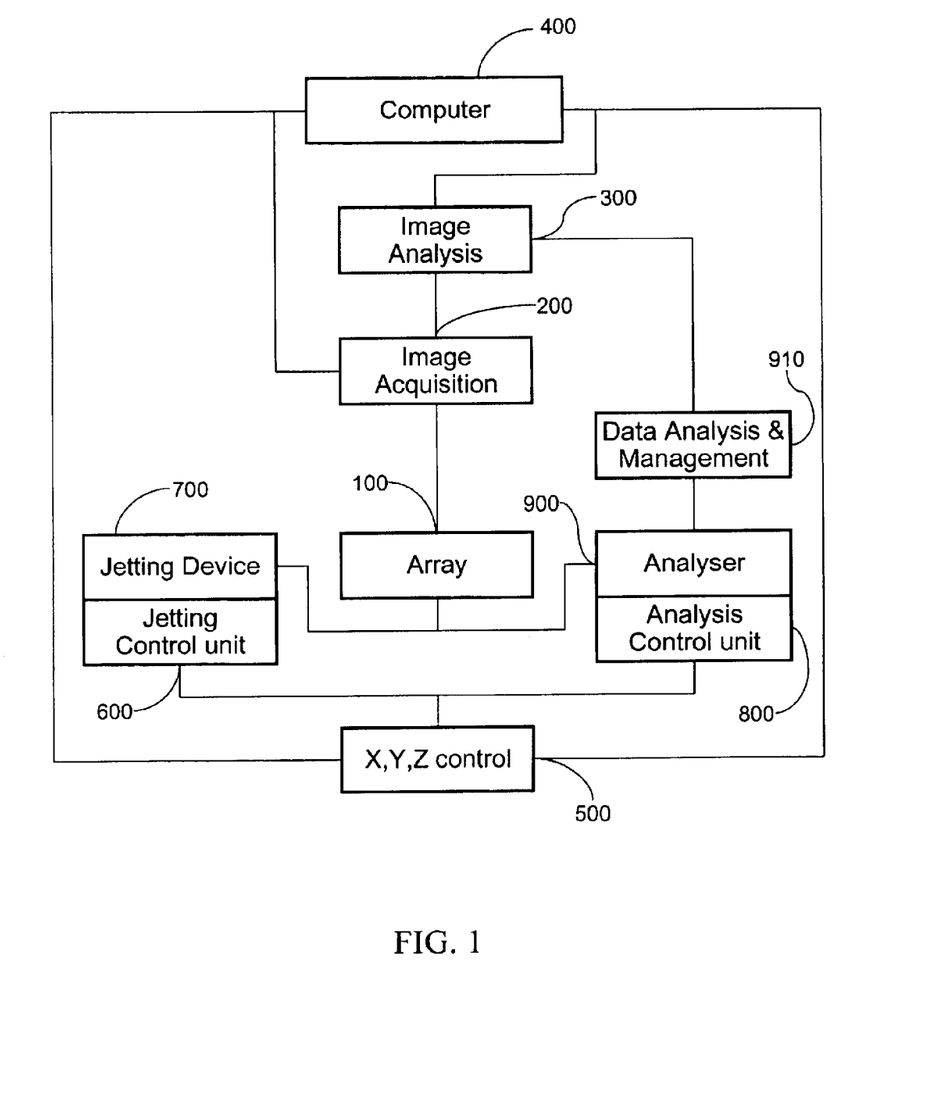
FIG. 1 is a schematic representation of a preferred embodiment of the present invention showing the process of obtaining information on an array of components or samples by way of acquiring or recording an image of the position of at least one component or sample in the array and utilizing the recorded image so as to allow the manipulation of the at least one component or sample in situ.

With reference to the drawings, FIG. 1 shows a schematic representation of one embodiment of the method according to the present invention. The system comprises an array 100, an image acquisition system 200, an image analysis system 300, a computer 400, an x, y, z adjustable platform 500, a plurality of chemical dispensing control units 600, a plurality of dispensing heads and reservoirs 700, an analyser control unit 800, an analyser 900, and a data analysis station 910.

The array 100 is positioned on or under the x, y, z adjustable table or arm 500 and an image 200 is acquired and transferred to the computer 400 as a digital image. This image is either interpreted by an image analysis system 300 where the coordinates of each component of the array are transformed to values that reflect the true x, y, z axes. Alternatively, the image stored in the computer 400 is used without interpretation and the coordinates of one particular component within the array 100 are used to move the x, y, z adjustable table or arm 500 which carries a dispensing head (etting device) 700. The dispensing head 700 is under the control of a chemical dispensing control unit 600 which is controlled by the computer 400 and dispenses a reagent onto the selected sample in the array 100. When the treatment has been completed, the coordinates of the treated component within the array 100 are used to move the x, y, z adjustable table or arm 500 which carries an analyser 900. The analyser 900 is under the control of an analysis control unit 800 which when selected by the operator via the computer 400 analyses treated selected sample 100. Data from the analysis is then collated by a data analysis and management system 910 which is correlated with the interpreted coordinates of each sample in the array from the image analysis system 300.

Figure 2:
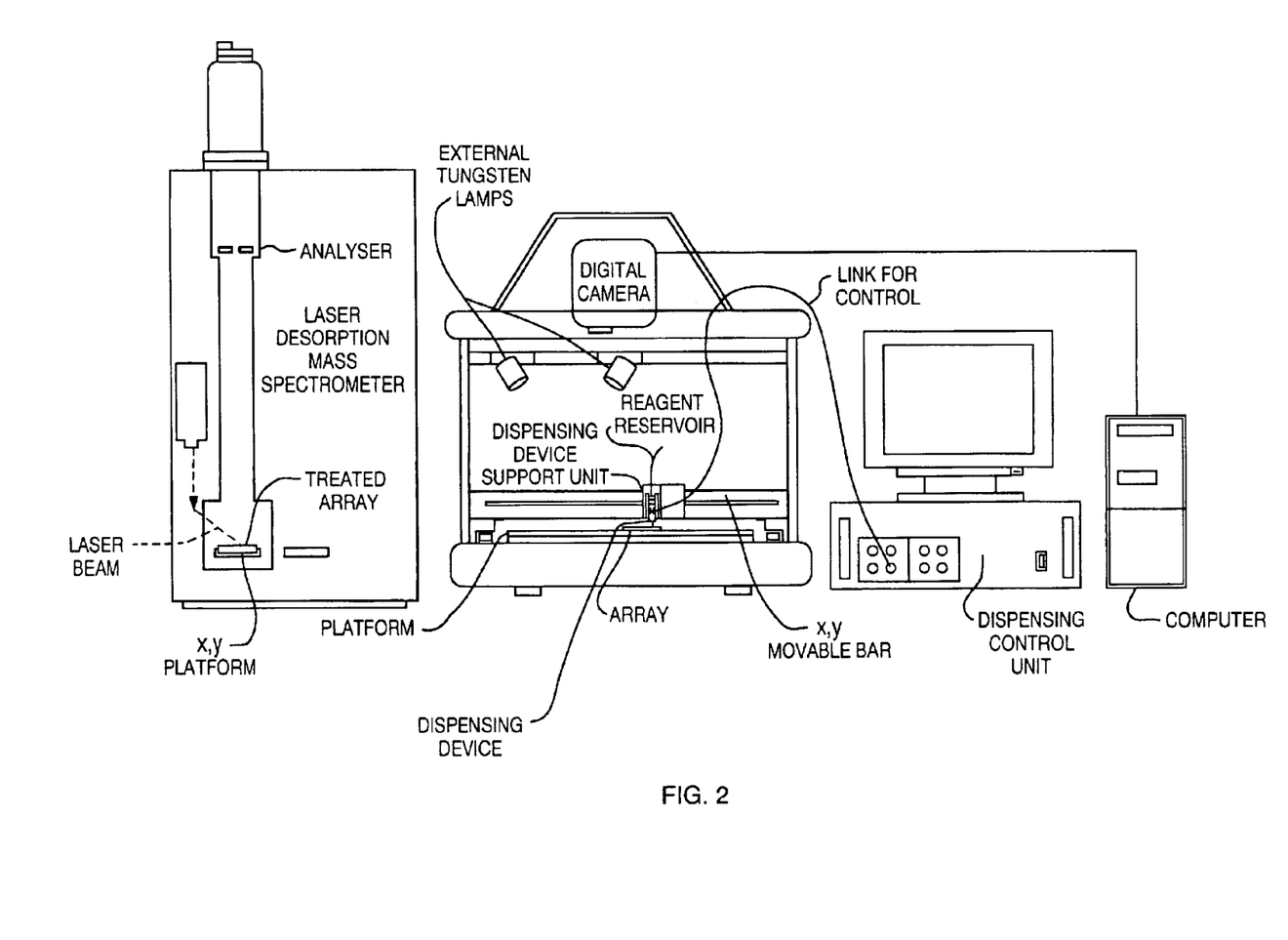
FIG. 2 is a schematic representation of a preferred embodiment of an apparatus according to the second aspect of the present invention for imaging, manipulating and analysing at least one component or sample of an array of components or samples.

In one embodiment of the method and apparatus according to the present invention, the x, y, z, adjustable platform, a chemical dispensing control unit, a dispensing head and reservoir, and an analyser, all under the control of a computer, is shown in FIG. 2. The array 102 is fixed onto a platform 502. The image of the array 102 is acquired via a digital camera 202. The array 102 is illuminated via a camera flash or external tungsten lamps 206. The image is transferred from the camera 202 to the computer 402. The image is processed and imported into "click-on-a-spot" software. This process translates the image pixel coordinates into robot coordinates. The "click-on-a-spot" software is then used to drive the dispensing device 702 to the selected sample in the array via an x, y movable bar 504. The z movement of the dispensing device 702 is via the dispensing device support unit 506. Reagent is dispensed from the reagent reservoir 508 via the computer control 402 of the chemical dispensing control unit 602 which is directly linked 604 to the dispensing device 702. The treated array 108 is then placed onto the x, y platform 806 of the analyser, in the example being a laser desorption mass spectrometer, 802. The x, y robotic coordinates are used to drive the analyser x, y platform 806 and position the treated sample directly in-line with the laser beam 804. The products of the treatment are then detected in the analyser 902.

Figure 3A:
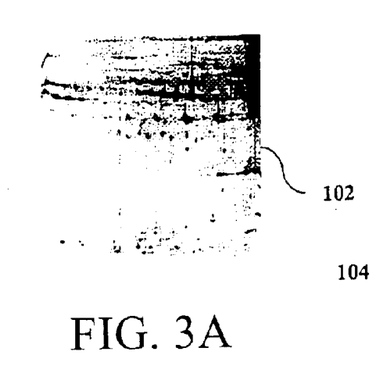
FIG. 3a is a schematic representation showing an image of an array in the form of an amido black stained two-dimensional polyacrylamide gel electrophoresis (2D-PAGE) separation of a protein mixture transferred to a polyvinylidene difluoride membrane.
Figure 3B:
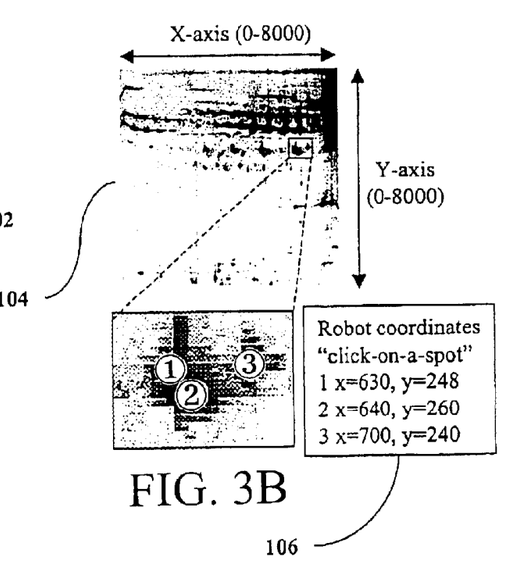
FIG. 3b is a schematic representation of the processed digital image of the array shown in FIG. 3a where the pixel coordinates have been transformed into coordinates for directing desired manipulation to a given sample. The inset highlights three selected proteins and their coordinates.
Figure 3C:
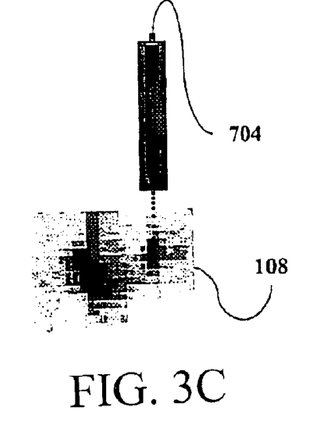
FIG. 3c is a schematic representation of the reagent-dispensing device being directed by the coordinates of the selected protein sample shown in FIG. 3b.
Figure 3D:
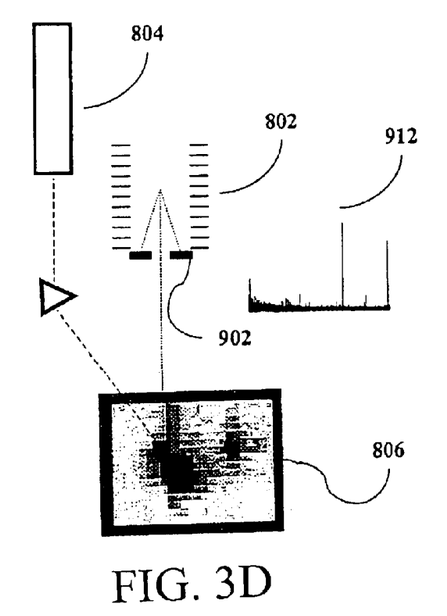
FIG. 3d is a schematic representation of the treated protein sample being directed by the coordinates to be "in-line" with a laser beam of a laser desorption mass spectrometer. The desorbed products are detected by a mass spectrometer and interpreted by the data management system.

An example of analysis of an array is shown in FIGS. 3a–3d. The array shown in FIG. 3a is a two-dimensional polyacrylamide gel electrophoresis separation of a mixture of proteins transferred onto a polyvinylidene membrane 102. The membrane is positioned and the image acquired by scanning and capturing as a digital image. The image is transferred to the computer and translated to pixel coordinates (FIG. 3b). An image of the array is now acquired by transforming the image pixel coordinates 104 into robotic coordinates 106. Protein samples positioned in the array can now be selected and the coordinates of the selected sample are used to drive a reagent dispensing device 704 to the selected protein sample where the reagent is dispensed. The treated sample on the array 108 is now moved to an analyser 802, the example shown is a matrix assisted laser desorption ionisation-time of flight (MALDI-TOF) mass spectrometer. The treated sample is positioned in-line with a laser beam 804 using the same robotic coordinates which drives the x, y table 806 of the mass spectrometer 802. The desorbed products of the treated sample are detected in the mass spectrometer 902 and the data is transformed in the data management system 912.

Figure 4A:
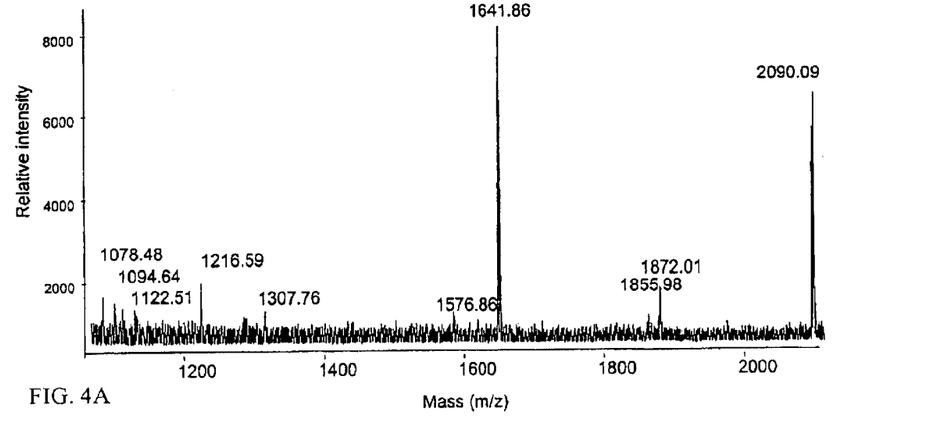
FIG. 4a shows a MALDI-TOF mass spectra of human alpha-1 antitrypsin peptides desorbed directly from PVDF membrane using a 337 nm nitrogen laser.

An example of trypsin treatment products desorbed off a polyvinylidene diflouride (PVDF) membrane of human serum proteins separated by 2D-PAGE is shown in FIG, 4a. The treatment involved applying a reagent ~3–4 $\mu$l digestion buffer (0.025 $\mu$g/$\mu$l Promega trypsin; 1% (v/v) reduced Triton X-100; 10% (v/v) MeCN; 5 mM Tris, pH 8.0). The treatment was left under humidified conditions for 3 hours at 37° C. The peptides were extracted by applying reagent buffer ~3–4 $\mu$l extraction buffer (70% (v/v) MeCN; 0.1% (v/v) TFA) onto the PVDF peptide sample. Before the extraction buffer was allowed to dry, a further aliquot of extraction buffer is applied. This was repeated 4–5 times.

Figure 4B:
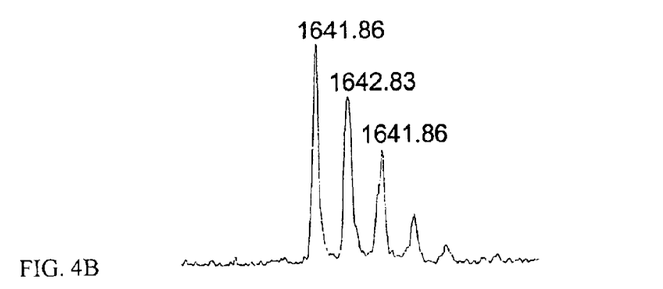
FIG. 4b shows detailed isotopic resolution of peptide 1641.86 m/z desorbed directly from PVDF membrane using a 337 nm nitrogen laser.
Figure 4C:
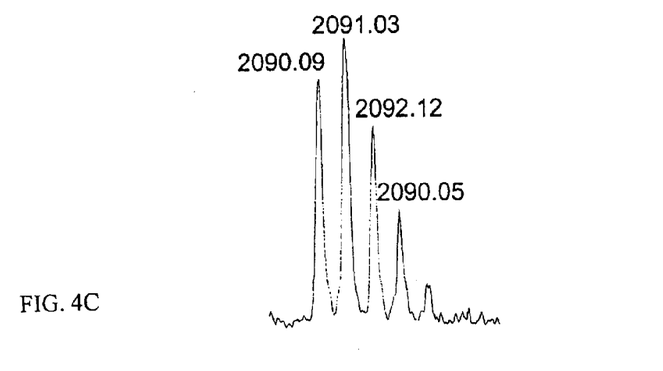
FIG. 4c shows detailed isotopic resolution of peptide 2090.09 m/z desorbed directly from PVDF membrane using a 337 nm nitrogen laser.

Finally, ~3–4 $\mu$l of reagent matrix solution, α-cyano-4-hydroxycinnamic acid matrix in 50% (v/v) MeCN:0.1% (v/v) TFA, was applied and allowed to air-dry. The treated PVDF membrane peptide sample was attached to the MALDI-TOF sample stage using double-sided sticking tape. The peptides were desorbed using 337 nm nitrogen laser and reflection delayed extraction mode. The quality of the data is represented by the isotopic resolution of two peptides, 1641.86 m/z and 2090.09 m/z, shown in FIGS. 4b and 4c respectively.

Figures 5A, 5B:
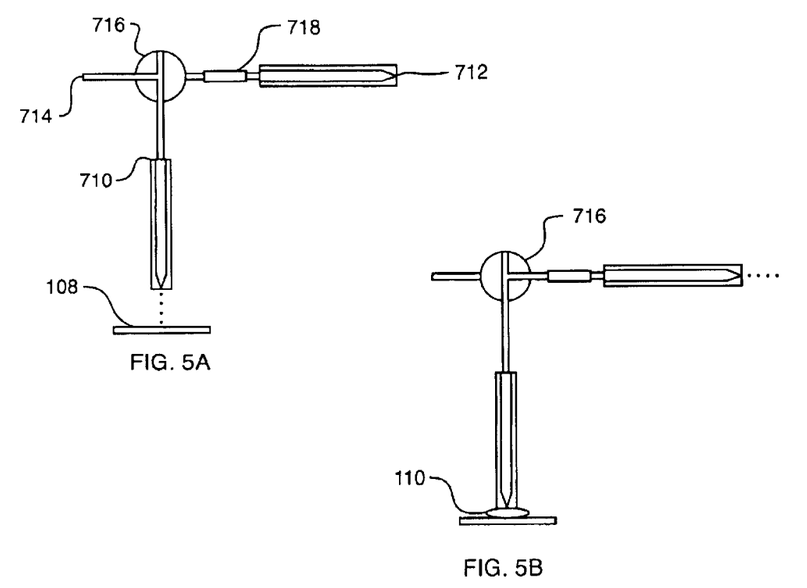
FIG. 5a is a schematic representation of a mechanism for delivering extraction solution reagent to a sample on an array.
FIG. 5b is a schematic representation of the mechanism for picking up a liquid sample from an array using a piezoelectric device.
Figure 5C:
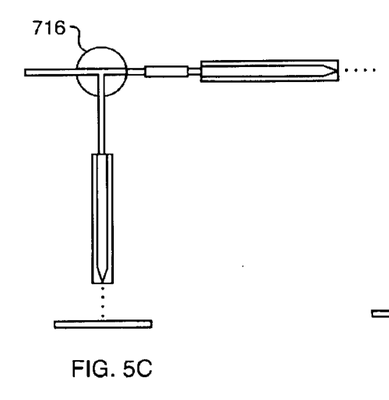
FIG. 5c is a schematic representation of a mechanism for washing a sample concentrated on a reversed phase packing support using a piezoelectric device.
Figure 5D:
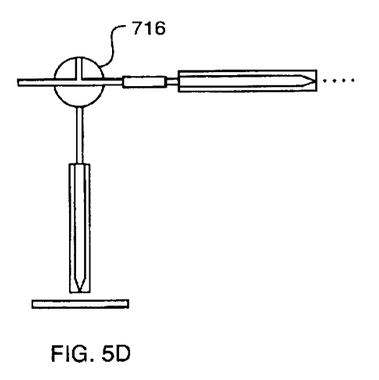
FIG. 5d is a schematic representation of the mechanism for eluting a sample concentrated on a reversed phase packing support using a piezoelectric device.
Figure 6A:
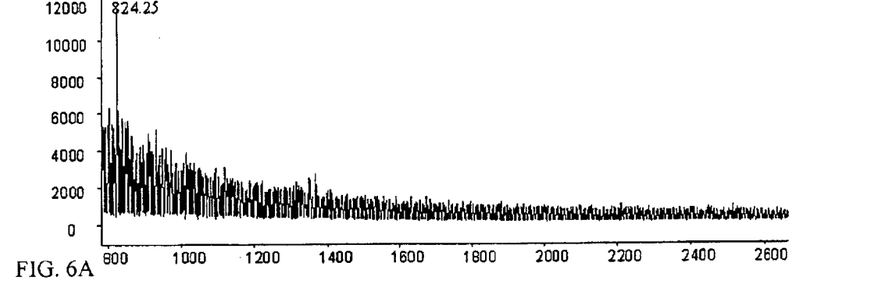
FIG. 6a is a MALDI-TOF mass spectrum representing a sample from the washing of the reversed phase packing support using a piezoelectric device.
Figure 6B:
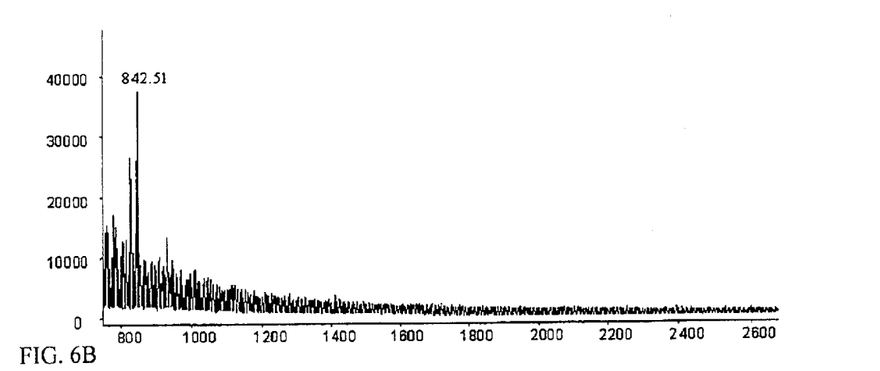
FIG. 6b is a MALDI-TOF mass spectrum representing the first peptide eluted from the reversed phase packing support using a piezoelectric device.
Figure 6C:
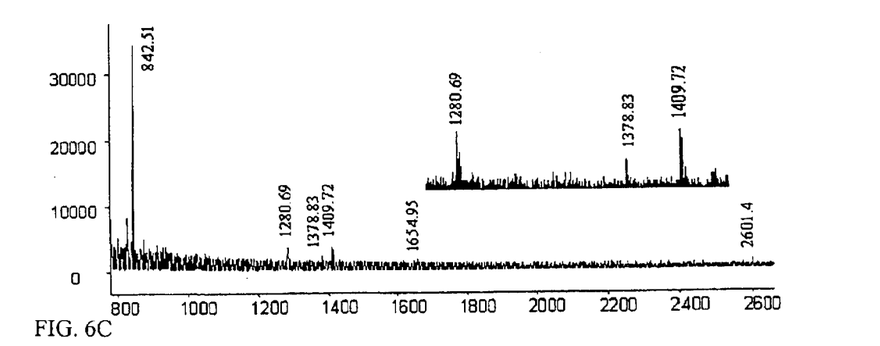
FIG. 6c is a MALDI-TOF mass spectrum representing a sample of peptides from the *Escherichia coli* protein outer membrane protein A, eluted from the reversed phase packing support using a piezoelectric device.

An example of a reagent delivery and extraction device for applying reagent and sampling reaction products from a treated sample is shown in FIG. 5a. A reagent, for example an extraction solution 714, is delivered through a 3-way valve 716 via a piezoelectric device 710 onto a sample on the array 108. This procedure may be repeated until sufficient sample is treated. The products from the treated sample 110 are then removed from the array by switching the 3-way valve in-line to a second piezoelectric device 712 which, in the example shown, is attached to a cartridge of reversed-phase chromatography packing 718 (FIG. 5b). Since the piezoelectric device has no moving internal parts the sample is picked up by activating device 712 while device 710 is lowered by Z-control into the sample 110. Following sample introduction onto the reversed-phase packing 718 where upon the reaction product is bound for analysis, the device 710 and the reversed-phase packing 718, are washed by switching the 3-way valve 716 to allow a suitable solvent to be delivered via the inlet 714 (FIG. 5c). It is not necessary to activate the devices for washing, as this can be done from a pressurised vessel attached to the valve 714. Alternatively, the washing can proceed by activating both devices. The sample is finally eluted from the reversed-phase packing 718 by introducing a suitable solvent attached to the valve inlet 714 by activating device 712 (FIG. 5d). Alternatively, the sample can be eluted from the reversed-phase packing 718 by introducing a suitable solvent, which is under pressure. The eluted product is then detected by some suitable means to allow its identification.

The invention relates particularly to the use of "ink jet" or other printing methods to dispense microdroplets of chemical reagents and/or proteins (such as enzymes and antibodies) onto proteins or other macromolecules which are immobilised or absorbed onto a substrate. The invention also relates in one preferred form to the use of mass spectrometry as a way of detecting/analysing the derivatives of the macromolecules following the chemical/enzyme reaction after application by the chemical printer.

In one example the method relates to a series of steps for protein analysis and is described as follows:

i) the proteins to be analysed are separated using a chromatographic technique, such as a polyacrylamide electrophoresis.

The proteins are visualised directly or transferred onto a support and visualised so that the protein pattern can be detected using a CCD camera and a digitised image obtained. It will be appreciated that protein spots can be visualised by a variety of methods including dyes, incorporation of a chemiluminescent or radiolabel and fluorescent derivatives.

ii) the image of the protein pattern is loaded into a software package where the individual protein spots/bands can be annotated. The image, or a subset of the image is then printed onto the original visualised support using the "ink jet" printing technology where the "ink" cartridges contain instead of ink appropriate chemicals, depending on the type of reaction desired. Where a chemistry requires the simultaneous delivery of two or more reagents, one can see how if the image was recorded or assigned one or more colours then a spot coloured green results in a reaction on that spot from the product of the chemicals in the blue and yellow cartridges. Here, one can immediately see that spots are derivatised in their immediate environment and the products of the chemical reaction will stay in that environment.

iii) the products from the individual chemical reactions must be analysed using a technique which can be directed at the protein spot. While it will be appreciated to one experienced in the art of protein analysis that the products of the printer can be analysed using a variety of chromatographic techniques, such as capillary electrophoresis, liquid chromatography and electrospray mass spectrometry, these techniques require the liquid extraction of the printed product prior to analysis. An alternative to the liquid extraction would be the use of laser desorption ionisation-time of flight (LDI-TOF) mass spectrometry. LDI-TOF mass spectrometry can detect both the product of the chemical/enzymic reaction (such as a modified amino acid from Edman chemistry or an oligosaccharide from a endoglycosidase digest) or the remaining substrate following the reaction (such as the shortened protein following Edman chemistry or the glycoprotein following release of the N-linked sugars). The analysis can occur in situ, where the support is transferred to a LDI-TOF and the laser is then guided to each spot using the digitised image of the original support. When necessary the protein pattern can be printed with a suitable matrix prior to analysis which assists the ionisation of the analyte: this is termed MALDI-TOF MS, matrix assisted laser desorption ionisation-time of flight mass spectrometry.

iv) If the analysis requires a further cycle of chemistry the membrane can be prepared for a second chemistry and printed again. This becomes the equivalent of an Edman sequenator but one which allows the sequencing of numerous proteins simultaneously.

The printer is computer controlled where the software allows selection of certain protein spots, much like a drawing program such as Corel Draw. The package, however, will have several preprogrammed methods for reduction and alkylation; endoproteinase digests; endoglycosidase digests and the Edman chemistry as these methods are routine in many laboratories and will be used frequently.

One example is the Edman chemistry, which is known to perform at high sensitivity on stained protein spots but must occur in a heated, anhydrous and oxygen free atmosphere. In this case, the printer should therefore be enclosed in such an environment. Four-colour ink jet technology allows precise mixing of reagents. Four reagents are necessary for Edman chemistry: R1 (which is phenylisothiocyanate or a isothiocyanate derivative in heptane or acetonitrile); R2 (coupling base); S1 (ethylacetate); and R3 (trifluoracetic acid). Following cleavage of the N-terminal amino acid, the support is moved to a laser desorption mass spectrometer where the released modified N-terminal amino acid is detected. The membrane is moved back to the chemical printer, washed with S1 on a vacuum manifold to remove the remaining released modified excess amino acid and a second round of chemistry starts. For those (blocked) proteins which produced no released amino acid, instead of a second cycle of Edman chemistry, these are subject to cleavage by for example Lys-C to produce peptides. In this way it is possible to develop a hierarchy of analyses that can be automated. This makes possible large scale analyses.

The laser desorption technology is preferable because, like the printer, it allows analysis in situ and in parallel. It should also be appreciated that the protein remaining can be subject to mass analysis, using a ladder-sequencing approach to identify the particular protein for which the mass is determined. It may be necessary in some cases to use a liquid extraction. The liquid extraction mechanism would also be driven by the image to extract the product from the correct spot.

In summary, the invention uses the concept of printing a "chemical" image of a molecule onto the same support which was used to first obtain the image. One way to print the chemicals is the "ink jet" technology.

(i) An image of the molecules to be studied is used as a template for printing a whole variety of selective chemistries on one, a sub-set, or all of the molecules. Hence, like a colour "ink jet" printer, the chemical printer can hold one or several different cartridges of chemicals that will move to the molecule and print the chemistry, or alternatively the support can be moved to the cartridge(s).

(ii) A derivative or reaction product of the "printed" molecule can be analysed while it is still absorbed on the support. Laser desorption ionisation technology and a mass spectrometer can be used as a detector to identify the derivative or reaction product. In the case of proteins studied by Edman chemistry, it is also possible to quantitate the amount of amino acids, hence measuring the abundance of the protein measured.

This aspect has been named "dry" analysis as it implies that the derivative does not first need to be extracted in a liquid from the support and subsequently identified. It remains possible, however, to use a liquid extraction into a suitable collection system or series of tubes as some derivatives may not be suitable for "dry" analysis.

(iii) Proteins that are absorbed onto a support are first visualised (termed the original support), by using a dye, fluorochrome or radiolabel for example. The original support is then scanned to obtain a digitised image which is exported into a software package where the digitised spots or sample positions can be manipulated. For example, by assigning a "colour" to the digitised spot or sample on the computer image, colour "ink jet" technology would allow the precise mixture of reagents from separate cartridges and the subsequent printing of these reagents onto the original support. An example of the use of the chemical printer is the identification of particular enzymes where an enzyme substrate cartridge is substituted for the yellow cartridge and an indicator which detects the product from the reaction is in the blue cartridge. Hence, when the chemical printer is instructed to print a green spot onto the original support any substrate reactions will be detected by a specific indicator (for example the reduced form of methyl-thiazolyl blue produces a purple formazan dye). The whole process can be repeated, for example by printing purple the red and blue cartridges are used which introduces a new substrate.

The present methods are particularly adaptable for automated control and large scale applications.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for analysing at least one sample in an array of samples, comprising:
   (a) recording an image of the position of the at least one sample relative to the other samples in the array;

(b) utilizing the recorded image in the application of a reagent or a succession of reagents to the at least one sample in situ; and (c) analysing the at least one sample for a reaction to or with the reagent or the succession of reagents.

2. The method according to claim 1 wherein the samples in the array of samples are biomolecules selected from the group consisting of proteins, peptides, saccharides, lipids, nucleic acid molecules, glycoproteins, complex carbohydrates, lipids and mixtures thereof.

3. The method according to claim 2 wherein the biomolecules are separated by chromatography to form an array of samples.

4. The method according to claim 3 wherein the chromatography is electrophoresis.

5. The method according to claim 4 wherein the electrophoresis is polyacrylamide gel electrophoresis.

6. The method according to claim 5 wherein the polyacrylamide gel electrophoresis is one dimension electrophoresis.

7. The method according to claim 6 wherein the one dimension electrophoresis is selected from the group consisting of isoelectric focusing, native polyacrylamide gel electrophoresis, and sodium dodecyl sulfate polyacrylamide gel electrophoresis.

8. The method according to claim 5 wherein the polyacrylamide gel electrophoresis is carried out in two dimensions.

9. The method according to claim 8 wherein the first dimension is by isoelectric focusing and the second dimension is by sodium dodecyl sulfate polyacrylamide gel electrophoresis.

10. The method according to claim 4 wherein the biomolecules separated by electrophoresis are transferred to a solid support.

11. The method according to claim 10 wherein the solid support is a membrane selected from the group consisting of polyvinylidene difluoride, nitrocellulose, nylon, polypropylene, polytetrafluoroethylene, and derivatised forms thereof having one or more functional groups.

12. The method according to claim 10 wherein the biomolecules transferred to the solid support are visualised by association with a dye, fluorescent group or metal, or by association with a second biomolecule which is coupled with a third biomolecule, dye, fluorescent group, or metal.

13. The method according to claim 1 wherein the array of samples is in a plane in order to assist in the recording of the image.

14. The method according to claim 13 wherein the image is recorded as an electronic or digital image.

15. The method according to claim 13 wherein the image is generated from a scan of the samples stained or illuminated to allow the samples to be visualised and the application of the reagent or the succession of reagents is carried out using a chemical printer application system where the reagent or the succession of reagents are discharged to a desired sample by the chemical printer application system.

16. The method according to claim 13 wherein the analysing is by liquid chromatography, photoelectrical, photochemical, laser, radiochemical, or mass spectral analyses.

17. The method according to claim 1 wherein the image is recorded as an electronic or digital image.

18. The method according to claim 17 wherein the image is generated from a scan of the samples stained or illuminated to allow the samples to be visualised and the application of the reagent or the succession of reagents is carried out using a chemical printer application system where the reagent or the succession of reagents are discharged to a desired sample by the chemical printer application system.

19. The method according to claim 17 wherein the analysing is by liquid chromatography, photoelectrical, photochemical, laser, radiochemical, or mass spectral analyses.

20. The method according to claim 1 wherein the image is generated from a scan of the samples following staining or illumination of the samples to allow the samples to be visualised and the application of the reagent or a succession of reagents is carried out using a chemical printer application system where the reagent or reagents are discharged to a desired sample by the chemical printer application system.

21. The method according to claim 1 wherein the steps (a) and (b) are repeated or cycled so as to carry out a series of manipulations of the same sample or a number of different samples in the array.

22. The method according to claim 21 wherein the series of manipulations are with the same reagent, the same set of reagents, or a number of different reagents.

23. The method according to claim 21 wherein the analysing is by liquid chromatography, photoelectrical, photochemical, laser, radiochemical, or mass spectral analyses.

24. The method according to claim 1 wherein the analysing is by liquid chromatography, photoelectrical, photochemical, laser, radiochemical, or mass spectral analyses.

25. The method according to claim 24 wherein the at least one sample is analysed directly for a given reaction product.

26. An apparatus for analysing at least one sample in an array of samples, the apparatus including:

(a) means for recording an image of the position of the at least one sample relative to the other samples in the array;

(b) means for applying a reagent or sequence of reagents to the at least one sample in situ;

(c) means for analysing the at least one sample for a reaction to or with the reagent or the sequence of reagents; and (d) control means for means (b), wherein means (b) applies the reagent or the sequence of reagents to the at least one sample according to the position of the at least one sample relative to the other samples in the array determined by means (a).

27. The apparatus according to claim 26 further including means for recording the analysis results obtained by means (c).

28. The apparatus according to claim 27 wherein means (b) is a chemical printer adapted to apply one or more reagents to the at least one sample.

29. The apparatus according to claim 27 wherein means (c) is selected from the group consisting of liquid chromatograph, photoelectrical detector, photochemical detector, laser detector, radiochemical detector, and mass spectrometer.

30. The apparatus according to claim 26 wherein means (a) is selected from the group consisting of scanner, photodetector, and charged coupled device.

31. The apparatus according to claim 30 wherein means (b) is a chemical printer adapted to apply one or more reagents to the at least one sample.

32. The apparatus according to claim 30 wherein means (c) is selected from the group consisting of liquid chromatograph, photoelectrical detector, photochemical detector, laser detector, radiochemical detector, and mass spectrometer.

33. The apparatus according to claim 26 wherein means (b) is a chemical printer adapted to apply one or more reagents to the at least one sample.

34. The apparatus according to claim 33 wherein means (c) is selected from the group consisting of liquid chromatograph, photoelectrical detector, photochemical detector, laser detector, radiochemical detector, and mass spectrometer.

35. The apparatus according to claim 26 wherein means (b) is a reagent delivery and extraction device including a fluid source, a fluid control means, a fluid delivery and sampling device for delivering fluid to a sample in the array and for sampling fluid applied to the sample on the array;

wherein means (c) comprises an extraction device for retaining a reaction product from a sample on the array; and wherein control means (d) comprises a control device for controlling fluid movement from the fluid source to the fluid delivery and sampling device and for controlling fluid movement from the sample to the extraction device via the fluid delivery and sampling device;

wherein, when the apparatus is in use, fluid capable of producing a reaction product from a sample is applied to a sample on the array from the fluid source via the fluid control means to the fluid delivery and sampling device by the action of the control device; and wherein a portion of the fluid applied to the sample is drawn through the fluid delivery and sampling device to the extraction device by the action of the control device.

36. The apparatus according to claim 35 wherein the fluid control means is a 3-way valve.

37. The apparatus according to claim 35 wherein the control device comprises a first control device for the fluid delivery and sampling device and a second control device for the extraction device.

38. The apparatus according to claim 37 wherein the first and second control devices are piezoelectric control devices.

39. The apparatus according to claim 35 wherein the fluid is a reagent for reacting with a sample to produce a detectable product capable of being retained by the extraction device.

40. The apparatus according to claim 35 wherein the extraction device is a cartridge of chromatography packing.

41. The apparatus according to claim 26 wherein means (c) is selected from the group consisting of liquid chromatograph, photoelectrical detector, photochemical detector, laser detector, radiochemical detector, and mass spectrometer.

42. The apparatus according to claim 26 wherein control means (d) is a computer programmed to control means (b).

43. The apparatus according to claim 26 wherein the array of samples is on a semi-solid or substantially solid support.

44. The apparatus according to claim 43 herein the at least one sample analysed has an area less than 100 mm$^2$.

45. The apparatus according to claim 43 wherein the at least one sample analysed has an area less than 50 mm$^2$.

46. The apparatus according to claim 43 wherein the at least one sample analysed has an area of 1 to 10 mm$^2$.

* * * * *